United States Patent [19]

Kanda et al.

[11] Patent Number: 5,187,186

[45] Date of Patent: Feb. 16, 1993

[54] PYRROLOINDOLE DERIVATIVES

[75] Inventors: Yutaka Kanda, Houston, Tex.; Youichi Uosaki, Machida, Japan; Hiromitsu Saito, Sagamihara, Japan; Hiroshi Sano, Machida, Japan; Eiji Kobayashi, Shizuoka, Japan; Makoto Morimoto; Satoru Nagamura, both of Machida, Japan

[73] Assignee: Kyowa Hakko Kogyo Co., Ltd., Tokyo, Japan

[21] Appl. No.: 755,760

[22] Filed: Sep. 6, 1991

Related U.S. Application Data

[62] Division of Ser. No. 545,579, Jun. 29, 1990, Pat. No. 5,070,092.

[30] Foreign Application Priority Data

Jul. 3, 1989 [JP] Japan ............................ 1-171605

[51] Int. Cl.⁵ .................... A61K 31/40; C07D 487/08
[52] U.S. Cl. ............................ 514/410; 548/421
[58] Field of Search ..................... 548/421; 514/410

[56] References Cited

U.S. PATENT DOCUMENTS 4,169,888 10/1979 Hanka et al. .................. 424/121
4,912,227 3/1990 Kelley et al. .................. 548/433
5,070,092 12/1991 Kanada et al. ................. 514/253

FOREIGN PATENT DOCUMENTS 0154445 9/1985 European Pat. Off. .
0271581 6/1988 European Pat. Off. .
0318056 5/1989 European Pat. Off. .
0339682 11/1989 European Pat. Off. .
0351865 1/1990 European Pat. Off. .
0004659 6/1988 World Int. Prop. O. .

Primary Examiner—Mukund J. Shah
Assistant Examiner—E. Bernhardt
Attorney, Agent, or Firm—Fitzpatrick, Cella, Harper & Scinto

[57] ABSTRACT

DC-88A derivatives represented by the general formula:

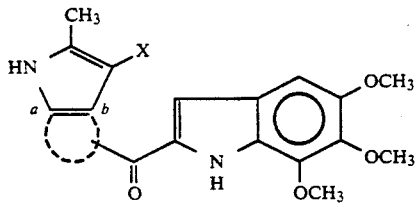

wherein X represents hydrogen or $CO_2R^1$ (in which $R^1$ represents hydrogen, a straight-chain or branched alkyl having 1 to 4 carbon atoms, allyl, or benzyl); and

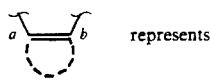 represents

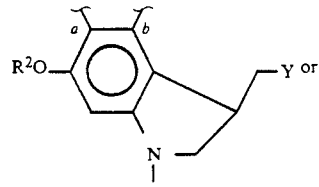 or

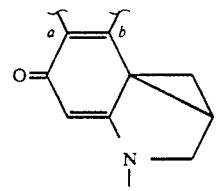

have an excellent anti-tumor activity and are useful as anti-tumor agents.

5 Claims, No Drawings

PYRROLOINDOLE DERIVATIVES

This application is a division of application Ser. No. 545,579, filed Jun. 29, 1990, now U.S. Pat. No. 5,070,092, issued Dec. 3, 1991.

BACKGROUND OF THE INVENTION

The present invention relates to novel DC-88A derivatives. The compounds have an excellent anti-tumor activity and are useful as anti-tumor agents.

WO 87/06265 discloses that DC-88A produced by microorganisms belonging to the genus Streptomyces exhibits not only antibacterial activity against various bacteria but also anti-tumor activity against lymphocytic leukemia P388, etc.

DC-88A has the following structure:

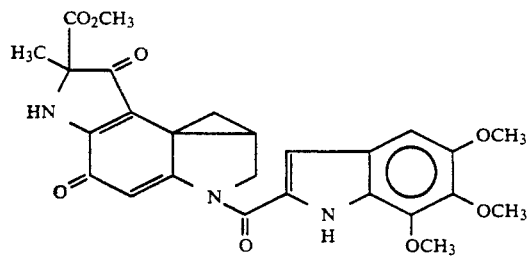

As the compounds having structures similar to that of DC-88A, DC-89A1 is disclosed in WO 87/06265 (EP-A-0271581) and DC-89A2, DC-89B1 and DC-89B2 are disclosed in Japanese Published Unexamined Patent Application No. 119787/90 (EP-A-0351865) and Japanese Published Unexamined Patent Application No. 139590/89. DC-89A1, DC-89A2, DC-89B1 and DC-89B2 have the following structures.

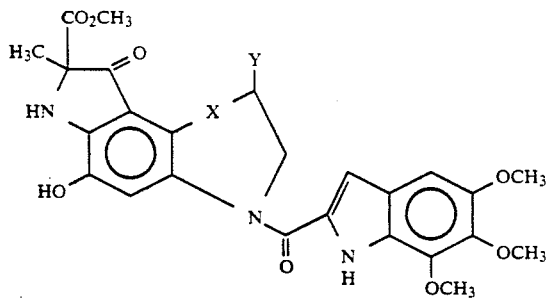

DC-89A1: $X=-CH_2-$, $Y=Cl$
DC-89A2: $X=$ single bond, $Y=-CH_2Cl$
DC-89B1: $X=-CH_2-$, $Y=Br$
DC-89B2: $X=$ single bond, $Y=-CH_2Br$ These compounds show antibacterial activity against various bacteria and anti-tumor activity against lymphocytic leukemia P388, etc.

Further, CC-1065, its derivatives and derivatives of SF2582C which are structurally similar to DC-88A and exhibit anti-tumor activity are disclosed in Japanese Published Unexamined Patent Application No. 64695/79 (U.S. Pat. No. 4,169,888), Japanese Published Unexamined Patent Application No. 193989/85 (EP-A-0154445) and Japanese Published Unexamined Patent Application No. 275581/89 (EP-A-0339681), respectively.

SUMMARY OF THE INVENTION

The present invention relates to compounds represented by general formula (A):

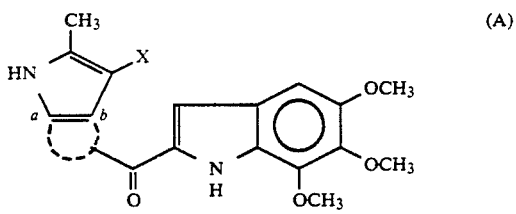

wherein X represents hydrogen or $CO_2R^1$ (in which $R^1$ represents hydrogen, a straight-chain or branched alkyl having 1 to 4 carbon atoms, allyl, or benzyl); and

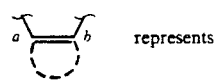 represents

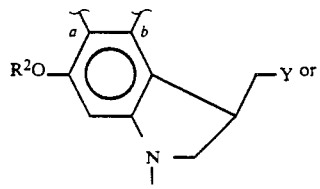

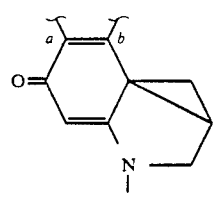

wherein Y represents chlorine or bromine; $R^2$ represents hydrogen, $COR^3$ (in which $R^3$ represents a straight-chain or branched alkyl having 1 to 4 carbon atoms), $CONR^4R^5$ (in which $R^4$ and $R^5$ independently represent a straight-chain or branched alkyl having 1 to 4 carbon atoms),

(in which n represents 4 or 5),

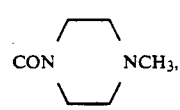

$CO_2R^6$ (in which $R^6$ represents a straight-chain or branched alkyl having 1 to 4 carbon atoms, or allyl), or $SiR^7R^8R^9$ (in which $R^7$, $R^8$ and $R^9$ independently represent a straight-chain or branched alkyl having 1 to 4 carbon atoms); or pharmceutically acceptable salts thereof.

The compounds represented by general formula (A) wherein

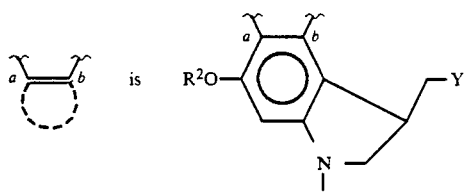 is 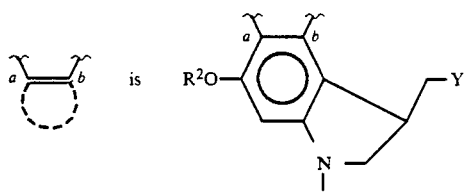

are hereinafter referred to as Compounds (I); and those represented by formula (A) wherein

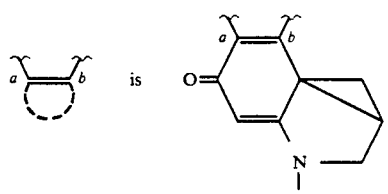 is 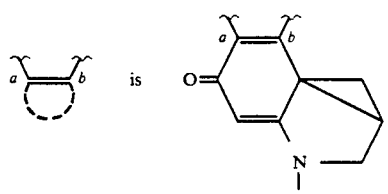

are referred to as Compounds (II).

In the definition of formula (A), the straight-chain or branched alkyl having 1 to 4 carbon atoms include, for example, methyl, ethyl, propyl, isopropyl, butyl, isobutyl, sec-butyl and tert-butyl.

As the pharmaceutically acceptable salts of Compounds (I) and (II), there are mentioned, for example, inorganic acid-addition salts such as hydrochloride, hydrobromide, hydroiodide, nitrate, sulfate and phosphate, as well as organic acid-addition salts such as acetate, benzoate, maleate, fumarate, succinate, tartrate, citrate, oxalate, glyoxalate, aspartate and methanesulfonate.

The processes for producing Compounds (I) and Compounds (II) are described below.

Compounds (I) and Compounds (II) can be obtained by the following steps, wherein Compounds (I-1) and (I-2) are included in the scope of Compounds (I) and Compounds (I-1)a are included in the scope of Compounds (I-1).

Step 1

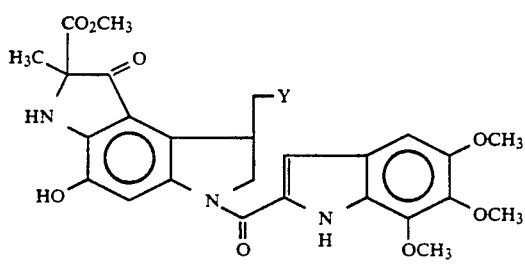

(Y = Cl: DC-89A2
Y = Br: DC-89B2)  Step 1

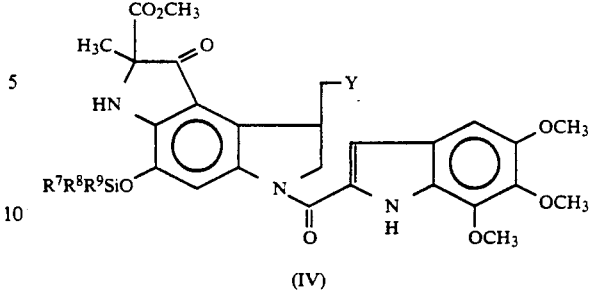

(IV)

In these formulae, Y, $R^7$, $R^8$ and $R^9$ have the same meanings as defined above.

Compound (IV) can be obtained by allowing DC-89A2 or DC-89B2 to react with Compound (III) represented by formula (III):

$$Cl-SiR^7R^8R^9 \quad \text{(III)}$$

(wherein $R^7$, $R^8$ and R9 have the same meanings as defined above) in an inert solvent in the presence of a base.

As the base, imidazole, potassium carbonate, potassium t-butoxide, triethylamine, etc. may be used. As the inert solvent, dimethylformaxide (DMF), tetrahydrofuran (THF), methylene chloride, acetonitrile, toluene, benzene, pyridine, etc. may be used singly or in combination. Compound (III) is used in an amount of 1 to 2 equivalents based on DC-89A2 or DC-89B2, and the base is also used in an amount of 1 to 2 equivalents. The reaction is usually carried out at $-30°$ C. to $50°$ C. and completed in 2 hours to one day.

Step 2

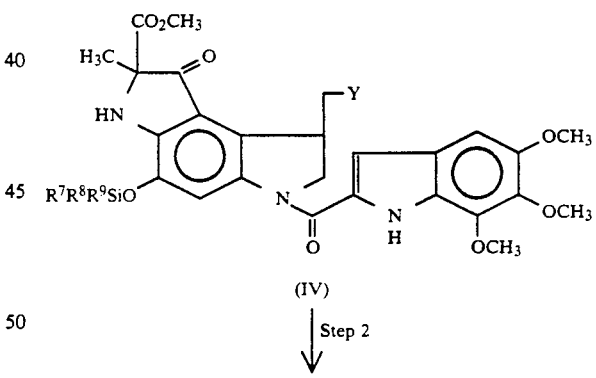

(IV)

Step 2

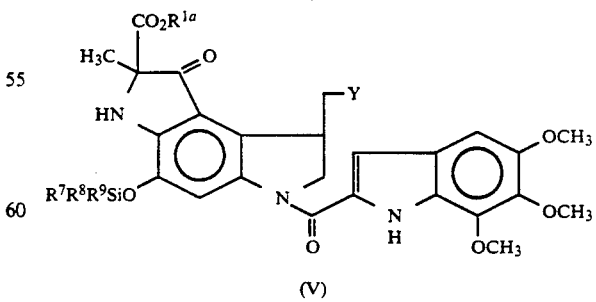

(V)

In these formulae, Y, $R^7$, $R^8$ and $R^9$ have the same meanings as defined above; and $R^{1a}$ has the same meaning as the above-mentioned $R^1$ excluding hydrogen atom.

Compound (V) can be obtained by allowing Compound (IV) to react with $R^{1a}OH$ in the presence of a base in an inert solvent or in the absence of a solvent.

As the inert solvent, methylene chloride, chloroform, THF, toluene, etc. may be used. As the base, potassium carbonate, sodium carbonate, sodium hydrogencarbonate, triethylamine, etc. are usually used in an amount of 0.1 to 2 equivalents based on Compound (IV). $R^{1a}OH$ is used in an amount of 2 equivalents based on Compound (IV), or in large excess of Compound (IV), when it serves also as a solvent in the reaction. The reaction is usually carried out at $-20°$ C. to $40°$ C. and completed in one hour to 3 days.

Step 3

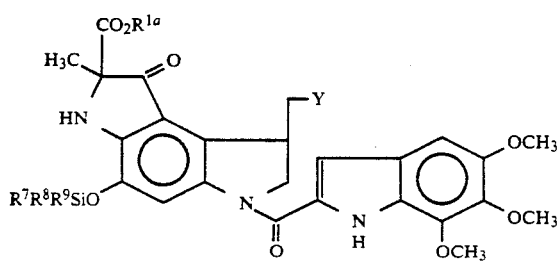

(V)

Reducing agent | Step 3

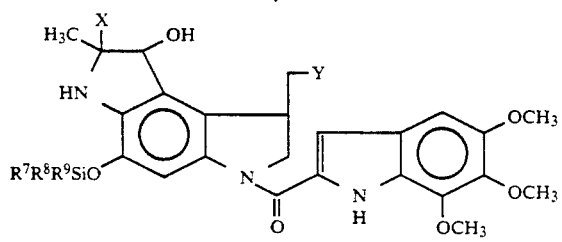

(VI): X = $CO_2R^{1a}$
(VII): X = H

In these formulae, Y, $R^{1a}$, $R^7$, $R^8$ and $R^9$ have the same meanings as defined above.

Compound (VI) and/or Compound (VII) can be obtained by reducing Compound (V) in an inert solvent.

Examples of the reducing agent include $NaBH_4$, $NaBH_3CN$, $LiAl[OC(CH_3)_3]_3H$, $Al[CH_2CH(CH_3)_2]_2H$ and $NaAl(OCH_2CH_2OCH_3)_2H_2$, which are usually used in an amount of 1 to 30 equivalents based on Compound (V). As the inert solvent, water, methanol, ethanol, t-butanol, THF, diethyl ether, toluene, etc. may be used singly or in combination. The reaction is carried out at $-50°$ C. to $80°$ C. and completed in one hour to one day.

Step 4

(VI), (VII)

| Step

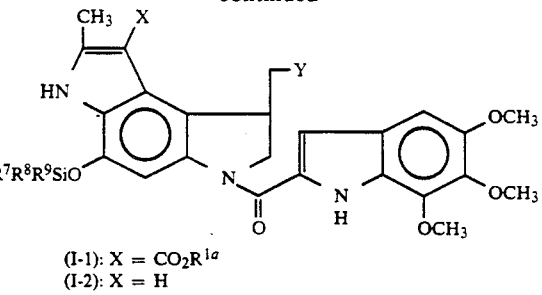

(I-1): X = $CO_2R^{1a}$
(I-2): X = H

In these formulae, Y, $R^{1a}$, $R^7$, $R^8$ and $R^9$ have the same meanings as defined above.

Compound (I-1) and Compound (I-2) can be obtained by allowing Compound (VI) and Compound (VII) to react with an acid in an inert solvent, respectively.

As the inert solvent, methylene chloride, chloroform, THF, ether, toluene, benzene, etc. may be used singly or in combination. Examples of the acid include methane-sulfonic acid, p-toluenesulfonic acid, camphorsulfonic acid, sulfuric acid, boron trifluoride-diethyl ether complex, aluminum chloride and zinc chloride, which are usually used in an amount of 0.1 to 3 equivalents based on Compound (VI) or (VII). The reaction is carried out at $0°$ C. to $80°$ C. and completed in one hour to 10 hours.

Step 5

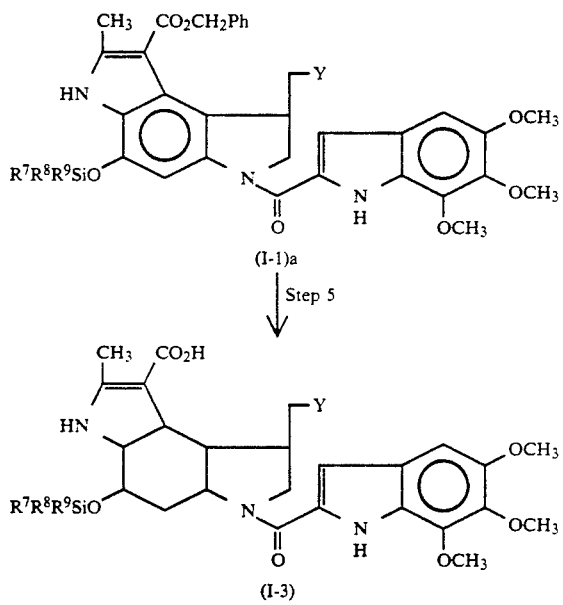

In these formulae, Y, $R^7$, $R^8$ and $R^9$ have the same meanings as defined above; and Ph represents phenyl.

Compound (I-3), wherein $R^{1a}$ is hydrogen, can be obtained by subjecting Compound (I-1)a, which is Compound (I-1) wherein $R^{1a}$ is benzyl to hydrogenolysis in an inert solvent.

As the inert solvent, methanol, ethanol, THF, dioxane, ethyl acetate, etc. can be used singly or in combination. As a catalyst for hydrogenolysis, palladium-carbon, palladium-barium sulfate, Raney nickel, etc. may be used in an amount of 10 to 50% by weight based on Compound (I-1)a. The reaction is usually carried out at $0°$ C. to $60°$ C. and completed in one hour to one day.

Step 6

(I-1), (I-2), (I-3)

↓ Step 6

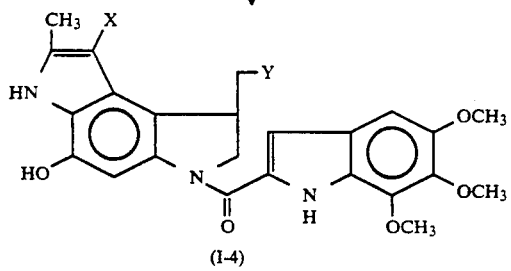

(I-4)

In the formula, X and Y have the same meanings as defined above. Compound (I-4) can be obtained by allowing Compound (I-1), (I-2) or (I-3) to react with a fluorine compound such as tetrabutylammonium fluoride or cesium fluoride in an inert solvent and then treating the product with hydrochloric acid or hydrobromic acid.

As the inert solvent, THF, acetonitrile, methylene chloride, methanol, ethanol, toluene, water, etc. may be used singly or in combination. The fluorine compound is usually used in an amount of 1 to 3 equivalents based on Compound (I-1), (I-2) or (I-3). Hydrochloric acid or hydrobromic acid is used in an amount of 3 equivalents to a large excess based on Compound (I-1), (I-2) or (I-3). The reaction is usually carried out at −20° C. to 60° C. and completed in one to 12 hours.

Step 7

(I-4)

↓ Step 7

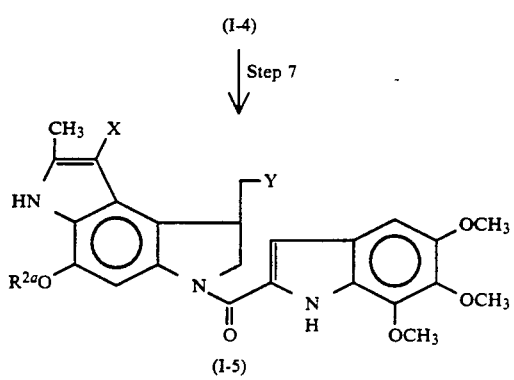

(I-5)

In the formula, X and Y have the same meanings as defined above; and $R^{2a}$ has the same meaning as the above-defined $R^2$ excluding hydrogen and $SiR^7R^8R^9$.

Compound (I-5), which is Compound (I) wherein $R^2$ is $COR^3$, $CONR^4R^5$,

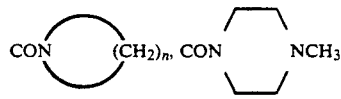

or $CO_2R^6$ (in which $R^3$, $R^4$, $R^5$, $R^6$ and n have the same meanings as defined above), can be obtained by allowing Compound (I-4) to react with the following Compound (VIII):

$R^{2a}$-Hal  (VIII)

wherein $R^{2a}$ has the same meaning as defined above; and Hal represents chlorine or bromine, in an inert solvent in the presence of a base. The desired compound wherein $R^{2a}$ is $COR^3$ can also be obtained by using an acid anhydride represented by $(R^3CO)_2O$ (in which $R^3$ has the same meaning as defined above).

Examples of the base include potassium carbonate, potassium t-butoxide, sodium hydride, triethylamine, dimethylaminopyridine and pyridine. As the inert solvent, DMF, THF, methylene chloride, acetonitrile, toluene, benzene, pyridine, etc. may be used singly or in combination. Compound (VIII) or the acid anhydride is used in an amount of 1 to 10 equivalents based on Compound (I-4), and the base is also used in an amount of 1 to 10 equivalents. The reaction is usually carried out at −30° C. to 50° C. and completed in 2 hours to one day.

Step 8

(I-4)

↓ Step 8

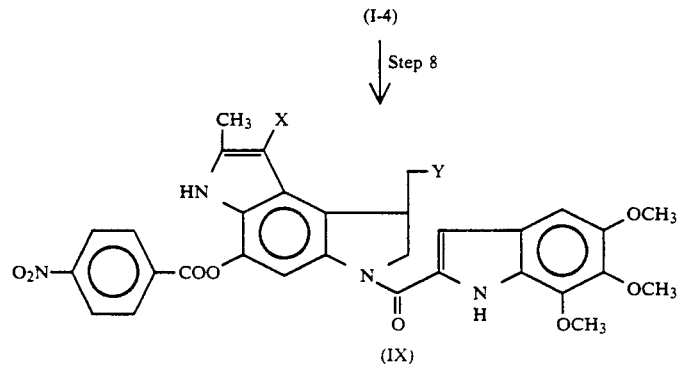

(IX)

In the formula, X and Y have the same meanings as defined above.

Compound (IX) can be obtained by allowing Compound (I-4) to react with p-nitrophenyl chloroformate in an inert solvent in the presence of a base.

Examples of the base include triethylamine, pyridine and 4-dimethylaminopyridine, which are usually used in an amount of 1 to 5 equivalents based on Compound (I-4). However, when the base acts also as a solvent, it is used in large excess of Compound (I-4). As the inert solvent, pyridine, methylene chloride, DMF, THF, toluene, etc. may be used singly or in combination. The p-nitrophenyl chloroformate is usually used in an amount of 1 to 5 equivalents based on Compound (I-4). The reaction is carried out at −10° C. to 50° C. and completed in 30 minutes to one day.

Step 9

(IX)

↓ Step 9

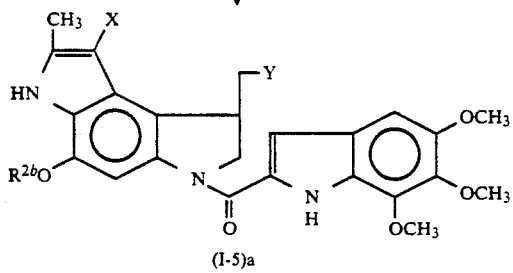

(I-5)a

In the formula, $R^{2b}$ represents $CONR^4R^5$,

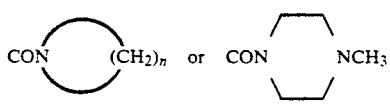

in the definition of $R^2$; and X, Y and n have the same meanings as defined above.

Compound (I-5)a can be obtained by allowing Compound (IX) to react with Compound (X) represented by $R^4R^5NH$,

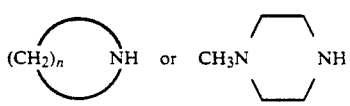

(in which $R^4$, $R^5$ and n have the same meanings as defined above) in an inert solvent.

As the inert solvent, pyridine, methylene chloride, DMF, THF, toluene, etc. may be used singly or in combination. Compound (X) is usually used in an amount of 1 to 5 equivalents based on Compound (IX). The reaction is carried out at −10° C. to 50° C. and completed in 30 minutes to one day.

Step 10

(I-4)

↓ Step 10

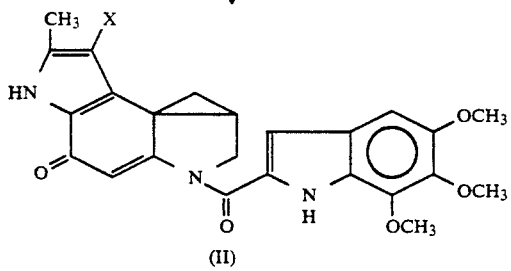

(II)

In the formula, X has the same meaning as defined above. Compound (II) can be obtained by treating Compound (I-4) with a base in an inert solvent.

As the inert solvent, acetonitrile, DMF, methylene chloride, THF, dimethylsulfoxide, etc. may be used singly or in combination. Examples of the base include triethylamine, diisopropylethylamine, potassium t-butoxide, 1,8-diazabicyclo[5.4.0]undeca-7-ene, potassium carbonate and sodium hydride, etc., which are usually used in an amount of 1 to equivalents based on Compound (I-4). The reaction is usually carried out at −20° C. to 50° C. and completed in 10 minutes to 5 hours.

Alternatively, Compound (II) can be obtained by the same process as Step 6 except that Compound (I-1), (I-2) or (I-3) is subjected to reaction without treatment with hydrochloric acid or hydrobromic acid.

Compound (II) can be converted into Compound (I-4) by treatment with hydrochloric acid or hydrobromic acid.

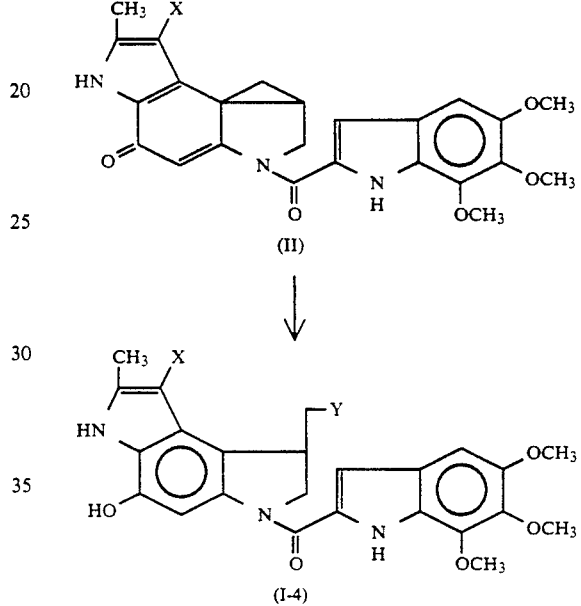

In the formulae, X and Y have the same meanings as defined above.

After completion of the reaction in each step, water, a buffer solution, hydrochloric acid, etc. may be added to the reaction mixture, if necessary, so as to stop the reaction, followed by extraction with a water-immiscible solvent such as ethyl acetate, chloroform or diethyl ether. The extract is washed with water, an aqueous solution of sodium hydrogencarbonate, a saturated aqueous solution of sodium chloride, etc. and dried over anhydrous sodium sulfate, etc., and then the solvent is distilled off. Alternatively, the reaction mixture may be concentrated and the residue is subjected to silica gel column chromatography, thin layer chromatography, high performance liquid chromatography, recrystallization, etc. to effect purification. Intermediates may be directly used in the subsequent reaction without being purified.

Compound (I), Compounds (II) and pharmaceutically acceptable salts thereof may be in the form of adducts with water or various solvents, which are also within the scope of the present invention.

The structures and compound numbers of representative compounds which fall under Compounds (I) and Compounds (II) are shown in Table 1. In Table 1, Type (I) and Type (II) respectively indicate that compounds fall under Compounds (I) and Compounds (II).

The structures and compound numbers of intermediates of the compounds of Table 1 are shown in Table 2.

TABLE 1

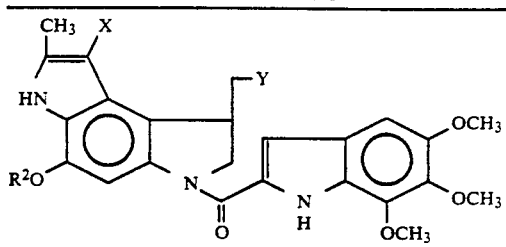
(I)

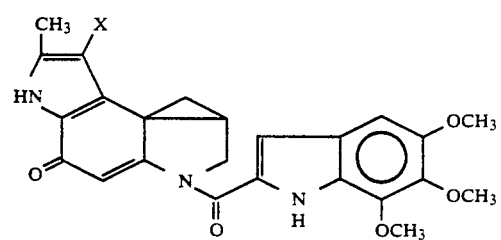
(II)

| Compound No. | Type | X | Y | R² |
|---|---|---|---|---|
| 1 | (I) | CO₂CH₃ | Br | (CH₃)₃CSi(CH₃)₂ |
| 2 | (I) | CO₂CH₃ | Cl | H |
| 3 | (I) | CO₂CH₃ | Br | H |
| 4 | (II) | CO₂CH₃ | — | — |
| 5 | (I) | H | Br | (CH₃)₃CSi(CH₃)₂ |
| 6 | (I) | H | Cl | H |
| 7 | (I) | H | Br | H |
| 8 | (II) | H | — | — |
| 9 | (I) | CO₂CHCH₃ \| CH₃ | Br | (CH₃)₃CSi(CH₃)₂ |
| 10 | (I) | CO₂CHCH₃ \| CH₃ | Cl | H |
| 11 | (II) | CO₂CHCH₃ \| CH₃ | — | — |
| 12 | (I) | CO₂CH₂Ph | Br | (CH₃)₃CSi(CH₃)₂ |
| 13 | (I) | CO₂CH₃ | Br | CON(CH₃)₂ |
| 14 | (I) | CO₂CH₃ | Br | CON⟨piperidine⟩ |
| 15 | (I) | CO₂CH₃ | Br | CON⟨azepane⟩ |
| 16 | (I) | CO₂CH₃ | Br | CON⟨N-CH₃-piperazine⟩ |
| 17 | (I) | CO₂CH₃ | Cl | CON(CH₃)₂ |
| 18 | (I) | CO₂CH₃ | Br | CON⟨N-CH₃-piperazine⟩·HCl |
| 19 | (I) | CO₂CH₃ | Cl | CON⟨N-CH₃-piperazine⟩ |
| 20 | (I) | CO₂CH₃ | Cl | CON⟨N-CH₃-piperazine⟩·HCl |

Note:
Ph means phenyl group.

TABLE 2

| Compound No. | X | Y | Z | R |
|---|---|---|---|---|
| a | CO₂CH₃ | H | OH | (CH₃)₃CSi(CH₃)₂ |
| b | H | H | OH | (CH₃)₃CSi(CH₃)₂ |
| c | CO₂CHCH₃ \| CH₃ | H | OH | (CH₃)₃CSi(CH₃)₂ |
| d | CO₂CH₂Ph | H | OH | (CH₃)₃CSi(CH₃)₂ |
| e | CO₂CH₃ | =O | | (CH₃)₃CSi(CH₃)₂ |

Note:
Ph means phenyl group.

The pharmaceutical activities of Compounds (I) and Compounds (II) are described below.

Growth Inhibitory Effect against HeLaS₃ Cells

HeLaS₃ cells were suspended in a medium comprising MEM medium, 10% fetal calf serum and 2 mM glutamine (hereinafter referred to as medium A) to a concentration of $3 \times 10^4$ cells/ml, and 0.1 ml of the suspension was put into each well of a 96-well microtiter plate.

After culturing at 37° C. overnight in a $CO_2$-incubator, 0.05 ml of a test sample appropriately diluted with medium A was added to each well.

The cells were further cultured for 72 hours in the $CO_2$-incubator and the culture supernatant was removed. The residue was washed once with phosphate buffered physiological saline (PBS), and 0.1 ml of medium A containing 0.02% Neutral Red was added to each well, followed by culturing at 37° C. for one hour in the $CO_2$-incubator to stain the cells. After removal of the culture supernatant, the cells were washed once with physiological saline, and the dye was extracted with 0.001N HCl/30% ethanol. Absorbance of the extract at 550 nm was measured with a microplate reader. By comparing the absorbance of the extract of intact cells with those of the cells treated with the test compound in known concentrations, the concentration of the test compound which inhibited growth of the cells by 50% ($IC_{50}$) was determined.

Therapeutic Effect against Sarcoma 180 Tumor Cells

Five male ddY-strain mice each having a weight of 18 to 20 g were used for each group as test animals, and $5 \times 10^5$ Sarcoma 180 tumor cells were implanted subcutaneously into the animals at the axilla. Ond day after the implantation, 0.2 ml of physiological saline containing a test compound in the concentration indicated in Table 3 was intravenously administered to each mouse. T/C[T: average tumor volume (mm$^3$) of the groups treated with the test compound, C: that of the control group which received an intravenous administration of 0.2 ml of physiological saline] was determined seven days after the implantation.

The results are shown in Table 3.

TABLE 3

| Compound No. | HeLaS$_3$ IC$_{50}$(nM) | Sarcoma 180 Dose (mg/kg) | T/C |
|---|---|---|---|
| 1 | 0.0020 | 0.25 | 0.043 |
| 2 | 0.00045 | — | — |
| 3 | <0.00024 | — | — |
| 4 | 0.0052 | 0.25 | 0.21 |
| 6 | 0.0019 | — | — |
| 7 | <0.00024 | — | — |
| 8 | 0.00040 | — | — |
| 13 | — | 1.0 | 0.063 |
| 14 | — | 1.0 | 0.098 |
|  |  | 0.50 | 0.20 |
| 15 | — | 1.0 | 0.088 |
|  |  | 0.50 | 0.21 |
| 16 | — | 0.50 | 0.24 |
| 18 | — | 0.50 | 0.14 |

(Note)
—: Not tested

Acute Toxicity Test

A test compound was intraperitoneally administered to dd strain male mice each weighing 20±1 g. MLD (the minimum lethal dose) was determined by observing the mortality for 14 days after the administration.

The results are shown in Table 4.

TABLE 4

| Compound No. | Acute Toxicity (MLD) mg/kg |
|---|---|
| 1 | 1.0 |
| 2 | 1.0 |
| 4 | 0.5 |
| 13 | 1.0 |
| 14 | 1.0 |
| 15 | 1.0 |
| 16 | 1.0 |
| 18 | 0.84 |

Compounds (I) and Compounds (II) may be used as anti-tumor agents singly or together with at least one pharmaceutically acceptable carrier. For example, Compounds (I), Compounds (II) or salts thereof are dissolved in a physiological saline solution or in an aqueous solution of glucose, lactose, mannitol, etc., to prepare a pharmaceutical composition suitable for injection. Alternatively, Compounds (I), Compounds (II) or salts thereof are freeze-dried in a conventional manner or mixed with sodium chloride to prepare a powder injection. The pharmaceutical composition may contain additives well known in the art of medical preparation, for example, pharmaceutically acceptable salts, if necessary. Although the doses of the composition may vary depending upon the age, condition, etc. of the patient, it is suitable to administer Compound (I) or Compound (II) in an amount of 0.00001 to 10 mg/kg/day for mammals including human beings. Administration may be made once a day (single administration or consecutive administration) or intermittently 1 to 3 times a week or once every 2 to 3 weeks, intravenously. If desired, oral administration is also possible in a similar dose and in a similar manner. Forms for oral administration include tablets, capsules, powders, granules and ampoules, which contain pharmaceutical auxiliaries well known in the art of medical preparation. If desired, intraarterial administration, intraperitoneal administration, intrathoracic administration, etc. may also be possible in a similar dose and in a similar manner.

The anti-tumor compositions of the present invention are expected to be effective against leukemia, gastric cancer, colon cancer, lung cancer, breast cancer, uterine cancer, etc. in mammals including human beings.

Certain specific embodiments of the present invention are illustrated by the following examples and reference examples.

The physicochemical properties of the compounds shown in the following examples and reference examples were determined with the following equipments.

| NMR | JEOL, Ltd. | FX-100 (100 MHz) |
|---|---|---|
|  | JEOL, Ltd. | PS-100 (100 MHz) |
|  | Bruker | AM-400 (400 MHz) |
| MS | Hitachi Ltd. | M-80B |
|  | Shimadzu | QP-1000 |
| IR | Nippon Bunko | IR-810 |

As the silica gel, Wakogel C-200 ® manufactured by Wako Pure Chemical Industries Co., Ltd. was used.

EXAMPLE 1

Synthesis of Compound 1

Compound (a) obtained in Reference Example 4 (110 mg, 0.16 mmol) was dissolved in chloroform, and 40 mg (0.17 mmol) of camphorsulfonic acid was added to the solution, followed by stirring at 50° C. for 2 hours and 40 minutes. After saturated aqueous sodium hydrogencarbonate was added to the reaction mixture, the mixture was extracted with chloroform. The chloroform layer was washed with a saturated aqueous solution of sodium chloride, dried over anhydrous sodium sulfate, and then concentrated under reduced pressure. The thus obtained crude product was purified by silica gel column chromatography (20 ml of silica gel, eluting solvent; n-hexane :ethyl acetate=3 :1 to 2 :1) to give 81 mg (yield 76%) of Compound 1.

The physicochemical properties of Compound 1 are as follows:

$^1$H-NMR (400 MHz, CDCl$_3$) δ(ppm): 9.40(1H, br. s), 8.30 (1H, br. s), 7.98(1H, s), 6.99(1H, d, J=2.3 Hz), 6.89(1H, s), 4.73(1H, m), 4.6–4.5(2H, m), 4.07 (3H, s), 3.98(3H, s), 3.95(3H, s), 3.92(3H, s), 3.81(1H, m), 3.21(1H, t, J=10.0 Hz), 2.76(3H, s), 1.07(9H, s), 0.39(3H, s), 0.37(3H, s)

IR (KBr) ν(cm$^{-1}$): 3466, 1697, 1628, 1493, 1414, 1306, 1111, 839

EIMS m/z: 687, 685(M$^{30}$), 592, 454, 452, 359, 234

EXAMPLE 2

Synthesis of Compound 2

Compound 1 (38 mg, 0.055 mmol) was dissolved in 10 ml of THF, and 2 ml of 0.2 M phosphate buffer (pH 4) and 0.55 ml (0.055 mmol) of 0.1 M THF solution of tetra-n-butylammonium fluoride were added to the solution, followed by stirring at 0° C. to room temperature for 4 hours. The reaction mixture was poured into 2N hydrochloric acid and the mixture was extracted with ethyl acetate. The ethyl acetate layer was washed successively with a saturated aqueous solution of sodium hydrogencarbonate and a saturated aqueous solution of sodium chloride, dried over anhydrous sodium sulfate, and then concentrated under reduced pressure. The thus obtained crude product was purified by silica gel column chromatography (10 ml of silica gel, eluting solvent; chloroform :methanol=97 :3) to give 28 mg (yield 97%) of Compound 2.

The Physicochemical properties of Compound 2 are as follows:

$^1$H-NMR (400MHz, CDCl$_3$)δ(ppm): 9.76(1H, br. s), 9.36 (1H, br. s), 9.05(1H, br. s), 8.30(1H, s), 7.00 (1H, d, J=2.2 Hz), 6.87(1H, s), 4.71(1H, m), 4.48 (2H, m), 4.10(3H, s), 3.97(3H, s), 4.0–3.8(1H, m), 3.923(3H, s), 3.916(3H, s), 3.30(1H, m), 2.67 (3H, s)

IR (KBr)ν(cm$^{-1}$): 3320, 2940, 1696, 1586, 1444, 1430, 1315, 1216, 1109

SIMS m/z: 528(M+1), 494, 294, 257, 234, 213

EXAMPLE 3

Synthesis of Compound 3

Compound 1 (52.9 mg, 0.077 mmol) was dissolved in 3.8 ml of THF, and 1.54 ml (0.15 mmol) of 0.1 N aqueous solution of sodium hydroxide was added to the solution, followed by stirring at room temperature for one hour. To the reaction mixture was added 5 ml of 1N hydrobromic acid, and the resulting mixture was extracted with ethyl acetate. The ethyl acetate layer was washed successively with a saturated aqueous solution of sodium hydrogencarbonate and a saturated aqueous solution of sodium chloride, dried over anhydrous sodium sulfate, and then concentrated under reduced pressure. The thus obtained crude product was purified by silica gel column chromatography (12 ml of silica gel, eluting solvent; n-hexane : ethyl acetate=1:2) to give 29.4 mg (yield 66%) of Compound 3.

The physicochemical properties of Compound 3 are as follows:

$^1$H-NMR (400MHz, CDCl$_3$)δ(ppm): 9.93(1H, br. s), 9.81 (1H, br. s), 9.24(1H, br. s), 8.35(1H, s), 6.95 (1H, d. J=2.1 Hz), 6.84(1H, s), 4.65(1H, d, J=10.0 Hz), 4.6–4.4(2H, m), 4.06(3H, s), 3.96(3H, s), 3.92(3H, s), 3.90(3H, s), 3.76(1H, dd, J=10.1, 2.5 Hz), 3.16(1H, t, J=9.8 Hz), 2.62(3H, s)

IR (KBr)ν(cm$^{-1}$): 3420, 2948, 1694, 1587, 1495, 1444, 1318, 1217, 1110

SIMS m/z: 574, 572(M+1), 257, 234

EXAMPLE 4

Synthesis of Compound 4

Compound 2 (13 mg, 0.025 mmol) was dissolved in 2 ml of acetonitrile, and 7.4 μl (0.049 mmol) of diazabicycloundecene was added to the solution, followed by stirring at room temperature for one hour. To the reaction mixture was added 0.2 M phosphate buffer (pH 4), and the resulting mixture was extracted with chloroform. The chloroform layer was washed successively with water and a saturated aqueous solution of sodium chloride, dried over anhydrous sodium sulfate, and then concentrated under reduced pressure. The thus obtained crude product was purified by silica gel column chromatography (10 ml of silica gel, eluting solvent; chloroform : methanol=98:2) to give 9.2 mg (yield 76%) of Compound 4.

The physicochemical properties of Compound 4 are as follows:

$^1$H-NMR (400MHz, CDCl$_3$)δ(ppm): 11.58(1H, br. s), 9.40 (1H, br. s), 7.12(1H, s), 6.95(1H, d, J=2.3 Hz), 6.81(1H, s), 4.45(2H, m), 4.08(3H, s), 3.90(3H, s), 3.82(3H, s), 3.67(1H, m), 2.63(3H, s), 2.38 (1H, dd, J=7.5, 3.4 Hz), 1.37(1H, t, J=4.2 Hz)

IR (KBr)ν(cm$^{-1}$): 3470, 3225, 2934, 1700, 1637, 1607, 1385, 1295, 1264, 1106

SIMS m/z: 494(M+3), 493, 492, 260, 234, 213

EXAMPLE 5

Synthesis of Compound 5

Compound 5 (22.9 mg, yield 77%) was obtained from 30.5 mg (0.047 mmol) of Compound (b) obtained in Reference Example 5 in a similar manner as in Example 1.

The physicochemical properties of Compound 5 are as follows:

$^1$H-NMR (100MHz, CDCl$_3$)δ(ppm): 9.44(1H, br. s), 7.90 (1H, br. s), 7.83(1H, s), 6.95(1H, d, J=2.4 Hz), 6.88(1H, s), 6.14(1H, q, J=1.1 Hz), 4.9–4.4(2H, m), 4.06(3H, s), 3.94(3H, s), 3.91(3H, s), 4.0–3.8(1H, m), 3.38(1H, t, J=10.3 Hz), 2.48(3H, s), 1.07(9H, s), 0.36(6H, s)

IR (KBr)ν(cm$^{-1}$): 3465, 2934, 1631, 1609, 1493, 1413, 1307, 839

EIMS m/z: 629, 627(M+), 547, 396, 394, 314, 313, 234, 73

EXAMPLE 6

Synthesis of Compound 6

Compound (b) (12 mg, 0.019 mmol) was dissolved in 3 ml of chloroform, and 4 mg (0.017 mmol) of camphorsulfonic acid was added to the solution, followed by stirring at room temperature for one hour. A saturated aqueous solution of sodium hydrogencarbonate was added to the reaction mixture, and the resulting mixture was extracted with chloroform. The chloroform layer was washed with a saturated aqueous solution of sodium chloride, dried over anhydrous sodium sulfate, and then concentrated under reduced pressure. The resulting residue was dissolved in 2 ml of THF, and 0.5 ml of water, 0.5 ml of 0.2 M phosphate buffer (pH 4) and 0.2 ml (0.02 mmol) of 0.1 M THF solution of tetra-n-butylammonium fluoride were added to the solution, followed by stirring at room temperature for 18 hours. The reaction mixture was poured into 2N hydrochloric acid and the mixture was extracted with ethyl acetate. The ethyl acetate layer was washed successively with a saturated aqueous solution of sodium hydrogencarbonate and a saturated aqueous solution of sodium chloride, dried over anhydrous sodium sulfate, and then concentrated under reduced pressure. The thus obtained crude product was purified by preparative silica gel thin layer chromatography (developer; chloroform : methanol=95 :5) to give 5.9 mg (yield 62%) of Compound 6.

The physicochemical properties of Compound 6 are as follows:

$^1$H-NMR (400MHz, CDCl$_3$)δ(ppm): 9.65(1H, br. s), 8.87 (1H, br. s), 8.48(1H, br. s), 8.14(1H, s), 6.99 (1H, d, J=2.5 Hz), 6.89(1H, s), 6.12(1H, q, J=1.0 Hz), 4.65(1H, dd, J=11.3, 9.1 Hz), 4.57(1H, dd, J=11.1, 3.7 Hz), 4.20(2H, m), 4.13(3H, s), 3.97 (3H, s), 3.92(3H, s), 3.52(1H, dd, J=11.3, 11.6 Hz), 2.45(3H, d, J=0.9 Hz)

IR (KBr)ν(cm⁻¹): 3350, 2938, 1608, 1495, 1388, 1312, 1220, 1105

EIMS m/z: 469(M⁺), 416, 234, 200

SIMS m/z: 470(M+1), 436, 434, 242, 234, 201

EXAMPLE 7

Synthesis of Compound 7

Compound 5 (22.7 mg, 0.036 mmol) was dissolved in 1.6 ml of THF, and 0.7 ml of 0.2 M phosphate buffer (pH 4) and 40 μl (0.040 mmol) of 1M THF solution of tetra-n-butylammonium fluoride were added to the solution, followed by stirring at room temperature for 6 hours. To the reaction mixture was added 2 ml of 1N hydrobromic acid, and after stirring for 5 minutes, the resulting mixture was extracted with dichloromethane. The dichloromethane layer was washed with a saturated aqueous solution of sodium chloride, dried over anhydrous sodium sulfate, and then concentrated under reduced pressure. The thus obtained crude product was purified by silica gel column chromatography (12 ml of silica gel, eluting solvent; chloroform : methanol=98 :2) to give 8.7 mg (yield 46%) of Compound 7.

The physicochemical properties of Compound 7 are as follows:

¹H-NMR (400MHz, CDCl₃)δ(ppm): 9.71 (1H, br. s), 8.92 (1H, br. s), 8.41(1H, br. s), 8.16(1H, m), 6.98 (1H, d, J=2.3 Hz), 6.88(1H, d, J=2.1 Hz), 6.11(1H, m), 4.8-4.6(1H, m), 4.6-4.5(1H, m), 4.11(3H, s), 4.1-3.9(2H, m), 3.96(3H, s), 3.92(3H, s), 3.38(1H, t, J=10.5 Hz), 2.44(3H, s)

IR (KBr)ν(cm⁻¹): 3406, 2936, 1604, 1495, 1429, 1313

SIMS m/z: 516, 514(M+1), 436, 434, 234, 201

EXAMPLE 8

Synthesis of Compound 8

Compound 5 (22.9 mg, 0.036 mmol) was dissolved in 2.3 ml of acetonitrile, and 55 μl (0.055 mmol) of 1 M THF solution of tetra-n-butylammonium fluoride was added to the solution, followed by stirring at room temperature for 2 hours. To the reaction mixture was added 0.1 M phosphate buffer (pH 7), and the resulting mixture was extracted with ethyl acetate. The ethyl acetate layer was washed with a saturated aqueous solution of sodium chloride, dried over anhydrous sodium sulfate, and then concentrated under reduced pressure. The thus obtained crude product was purified by silica gel column chromatography (12 ml of silica gel, eluting solvent; chloroform :methanol=99 :1) to give 14.9 mg (yield 94%) of Compound 8.

The physicochemical properties of Compound 8 are as follows:

¹H-NMR (400MHz, CDCl₃) δ (ppm): 9.99(1H, br. s), 9.31 (1H, br. s), 6.94(1H, d, J=2.3 Hz), 6.92(1H, s), 6.78(1H, s), 5.67(1H, m), 4.40(1H, dd, J=10.4, 4.5 Hz), 4.36(1H, d, J=10.3 Hz), 4.07(3H, s), 3.93 (3H, s), 3.89(3H, s), 2.69 (1H, m), 2.36(3H, s), 1.70(1H, m), 1.53(1H, t, J=4.6 Hz)

IR (KBr)ν(cm⁻¹): 3455, 3295, 2938, 1636, 1477, 1388, 1305, 1265

SIMS m/z: 436(M+3), 435, 434, 234, 202, 201

EXAMPLE 9

Synthesis of Compound 9

Compound 9 (37.5 mg, yield 70%) was obtained from mg (0.95 mmol) of Compound (c) obtained in Reference Example 6 in a similar manner as in Example 1.

The physicochemical properties of Compound 9 are as follows:

¹H-NMR (100MHz, CDCl₃) δ (ppm): 9.49(1H, br. s), 8.45 (1H, br. s), 8.02(1H, s), 7.01(1H, d, J=2.4 Hz), 6.90(1H, s), 5.33(1H, m), 4.9-4.5(3H, m), 4.1-3.8(1H, m), 4.05(3H, s), 3.94(3H, s), 3.91(3H, s), 3.24(1H, t, J=10.4 Hz), 2.73(3H, s), 1.44(6H, d, J=6.0 Hz), 1.07(9H, s), 0.36(6H, s)

EXAMPLE 10

Synthesis of Compound 10 and Compound 11

Compound 9 (37 mg, 0.052 mmol) was dissolved in ml of THF, and 0.5 ml of 0.5 M phosphate buffer (pH 4) and 0.52 ml (0.052 mmol) of 0.1 M THF solution of tetra-n-butylammonium fluoride were added to the solution under ice cooling, followed by stirring for one hour. The reaction mixture was poured into 2N hydrochloric acid and the mixture was extracted with ethyl acetate. The ethyl acetate layer was washed successively with a saturated aqueous solution of sodium hydrogencarbonate and a saturated aqueous solution of sodium chloride, dried over anhydrous sodium sulfate, and then concentrated under reduced pressure. The thus obtained crude product was purified by silica gel column chromatography (10 ml of silica gel, eluting solvent; n-hexane :ethyl acetate=2 :1) to give 11 mg (yield 38%) of Compound 10 and 12 mg (yield 44%) of Compound 11.

The physicochemical properties of Compound 10 are as follows:

¹H-NMR (400 MHz, CDCl₃)δ(ppm): 10.16(2H, br. s), 9.42 (1H, br. s), 8.44(1H, s), 6.94(1H, d, J=2.2 Hz), 6.82(1H, s), 5.26(1H, qq, J=6.3, 6.3 Hz), 4.67(1H, d, J=10.3 Hz), 4.55(1H, m), 4.43(1H, m), 4.1-3.8 (1H, m), 3.98(3H, s), 3.96(3H, s), 3.89(3H, s), 3.27(1H, t, J=10.2 Hz), 2.56(3H, s), 1.38(3H, d, J=6.3 Hz), 1.36(3H, d, J=6.3 Hz)

IR (KBr)ν(cm⁻¹): 3325, 1684, 1589, 1494, 1428, 1316, 1218, 1102

SIMS m/z: 556(M+1), 522, 323, 234, 213

The physicochemical properties of Compound 11 are as follows:

¹H-NMR (400MHz, CDCl₃)δ(ppm): 11.59(1H, br. s), 9.45 (1H, br. s), 7.12(1H, s), 6.96(1H, d, J=2.3 Hz), 6.81(1H, s), 5.16(1H, qq, J=6.3, 6.3 Hz), 4.45(2H, m), 4.07(3H, s), 3.94(3H, s), 3.90(3H, s), 3.69 (1H, m), 2.63(3H, s), 2.41(1H, dd, J=7.5, 3.3 Hz), 1.38(1H, m), 1.36(3H, d, J=6.3 Hz), 1.35(3H, d, J=6.2 Hz)

IR (KBr)ν(cm⁻¹): 3470, 3190, 1695, 1635, 1608, 1385, 1292, 1264, 1100

SIMS m/z: 522(M+3), 521, 520, 506, 289, 234, 213

EXAMPLE 11

Synthesis of Compound 12

Compound (d) obtained in Reference Example 7 (38.5 mg, 0.049 mmol) was dissolved in 3.9 ml of toluene, and 12.6 mg (0.054 mmol) of camphorsulfonic acid was added to the solution, followed by stirring at 50° C. for 5 hours. Sodium hydrogencarbonate was added to the reaction mixture, and the resulting mixture was extracted with chloroform. The chloroform layer was washed with a saturated aqueous solution of sodium chloride, dried over anhydrous sodium sulfate, and then concentrated under reduced pressure. The thus obtained crude product was purified by silica gel column chromatography (12 ml of silica gel, eluting solvent; n-hexane :ethyl acetate=5 :1) to give 30.4 mg (yield 80%) of Compound 12.

The physicochemical properties of Compound 12 are as follows:

$^1$H-NMR (100MHz, CDCl$_3$)$\delta$(ppm): 9.38(1H, br. s), 8.35 (1H, br. s), 7.92(1H, s), 7.6–7.2(5H, m), 6.92 (1H, d, J=2.2 Hz), 6.82(1H, s), 5.50 and5.28(2H, ABq, J=12.4 Hz), 4.8–4.4(3H, m), 4.00(3H, s), 3.89 (3H, s), 3.86(3H, s), 3.72(1H, m), 3.18(1H, t, J=9.4 Hz), 2.68(3H, s), 1.06(9H, s), 0.38(6H, s)

IR (KBr)$\nu$(cm$^{-1}$): 3460, 1696, 1628, 1418, 1308, 840

EIMS m/z: 763, 761(M+), 683, 591, 530, 528, 447, 358, 300, 234, 91

EXAMPLE 12

Synthesis of Compound 13

Compound 1 (50 mg, 0.073 mmol) was dissolved in 5 ml of THF, and 0.087 ml (0.087 mmol) of 1.0 M THF solution of tetra-n-butylammonium fluoride was added to the solution, followed by stirring at room temperature for one hour. To the reaction mixture was added 0.2 M phosphate buffer (pH 7), and the resulting mixture was extracted with chloroform. The chloroform layer was washed with a saturated aqueous solution of sodium chloride, dried over anhydrous sodium sulfate, and then concentrated under reduced pressure. Acetonitrile (5 ml) and 0.1 ml of 48% hydrobromic acid were added to the thus obtained crude product, followed by stirring at room temperature for 2 hours. To the reaction mixture was added 0.2 M citrate buffer (pH 4), and the resulting mixture was extracted with chloroform. The chloroform layer was washed with a saturated aqueous solution of sodium chloride, dried over anhydrous sodium sulfate, and then concentrated under reduced pressure. Pyridine (5 ml) and 0.067 ml (0.73 mmol) of N,N-dimethylcarbamoyl chloride were added to the thus obtained crude product at 0° C., followed by stirring at 0° C. to room temperature for 5 hours. To the reaction mixture was added 1N hydrochloric acid, and the resulting mixture was extracted with chloroform. The chloroform layer was washed successively with a saturated aqueous solution of sodium hydrogencarbonate and a saturated aqueous solution of sodium chloride, dried over anhydrous sodium sulfate, and then concentrated under reduced pressure. The thus obtained crude product was purified by silica gel column chromatography (20 ml of silica gel, eluting solvent; chloroform :methanol=100 :1) to give 32 mg (yield 67%) of Compound 13.

The physicochemical properties of Compound 13 are as follows:

$^1$H-NMR (400MHz, CDCl$_3$)$\delta$(ppm): 9.37(1H, br. s), 9.09 (1H, br. s), 8.14(1H, s), 7.00(1H, d, J=2.3 Hz), 6.90(1H, s), 4.73(1H, br. d, J=9.7 Hz), 4.58(2H, m), 4.08(3H, s), 3.97(3H, s), 3.95(3H, s), 3.92 (3H, s), 3.81(1H, dd, J=9.9, 2.3 Hz), 3.22(1H, dd, J=9.9, 9.9 Hz), 3.20(3H, s), 3.07(3H, s), 2.59(3H, s)

IR (KBr)$\nu$(cm$^{-1}$): 3470, 3300, 2946, 1701, 1411, 1313, 1217, 1167, 1109

SIMS m/z : 645, 643(M+1)+, 565, 411, 409, 234

EXAMPLE 13

Synthesis of Compound 14

Compound 1 (10 mg, 0.015 mmol) was dissolved in 2 ml of THF, and 0.020 ml (0.020 mmol) of 1.0 M THF solution of tetra-n-butylammonium fluoride was added to the solution, followed by stirring at room temperature for one hour. To the reaction mixture was added 0.2 M phosphate buffer (pH 7), and the resulting mixture was extracted with ethyl acetate. The ethyl acetate layer was washed with a saturated aqueous solution of sodium chloride, dried over anhydrous sodium sulfate, and then concentrated under reduced pressure. Acetonitrile (2 ml) and 1 ml of 1 M hydrobromic acid were added to the resulting crude product, followed by stirring at room temperature for one hour. To the reaction mixture was added 0.2 M citrate buffer (pH 4), and the resulting mixture was extracted with chloroform. The chloroform layer was washed with a saturated aqueous solution of sodium chloride, dried over anhydrous sodium sulfate, and then concentrated under reduced pressure. The thus obtained crude product was dissolved in 1 ml of dichloromethane, and 0.004 ml (0.029 mmol) of triethylamine and 1 ml of dichloromethane solution containing 6 mg (0.03 mmol) of p-nitrophenyl chloroformate were added to the solution at 0° C., followed by stirring at 0° C. for one hour. Then, 0.004 ml (0.045 mmol) of piperidine was added to the reaction mixture and the mixture was stirred at 0° C. to room temperature for 24 hours. To the reaction mixture was added 1N hydrochloric acid, followed by extraction with chloroform. The chloroform layer was washed successively with a saturated aqueous solution of sodium hydrocarbonate and a saturated aqueous solution of sodium chloride, dried over anhydrous sodium sulfate, and then concentrated under reduced pressure. The thus obtained crude product was purified by silica gel column chromatography (20 ml of silica gel, eluting solvent; n-hexane :ethyl acetate =1 :2) to give 6 mg (yield 58%) of Compound 14.

The physicochemical properties of Compound 14 are as follows:

$^1$H-NMR (400 MHz, CDCl$_3$)$\delta$(ppm): 9.38(1H, br. s), 9.09 (1H, br. s), 8.14(1H, s), 7.00(1H, d, J=2.4 Hz), 6.90(1H, s), 4.74(1H, dd, J=10.3, 1.0 Hz), 4.61 (2H, m), 4.07(3H, s), 3.96(3H, s), 3.95(3H, s), 3.92(3H, s), 3.81(1H, dd, J=9.9, 2.1 Hz), 3.69 (2H, br), 3.54(2H, br), 3.22(1H, dd, J=10.1, 10.1 Hz), 2.59(3H, s), 1.68(6H, br)

IR (KBr)$\nu$(cm$^{-1}$): 3470, 3250, 2940, 2858, 1698, 1491, 1410, 1312, 1255, 1214, 1165, 1109

SIMS m/z : 685, 683(M+1)+, 605, 234

EXAMPLE 14

Synthesis of Compound 15

Compound 1 (30 mg, 0.044 mmol) was dissolved in 6 ml of THF, and 0.053 ml (0.053 mmol) of 1.0 M THF solution of tetra-n-butylammonium fluoride was added to the solution, followed by stirring at room temperature for one hour. To the reaction mixture was added 0.2 M phosphate buffer (pH 7), and the resulting mixture was extracted with chloroform. The chloroform layer was washed with a saturated aqueous solution of sodium chloride, dried over anhydrous sodium sulfate, and then concentrated under reduced pressure. Acetonitrile (6 ml) and 3 ml of 1 M hydrobromic acid were added to the resulting crude product, followed by stirring at room temperature for one hour. To the reaction mixture was added 0.2 M citrate buffer (pH 4), and the resulting mixture was extracted with chloroform. The chloroform layer was washed with a saturated aqueous solution of sodium chloride, dried over anhydrous sodium sulfate, and then concentrated under reduced pressure. The thus obtained crude product was dissolved in 3 ml of dichloromethane, and 0.012 ml (0.088 mmol) of triethylamine and 3 ml of dichloromethane solution containing 17.6 mg (0.088 mmol) of p-nitrophenyl chloroformate were added to the solution at −10° C., followed by stirring at −10° C. to 0° C. for one hour. Then, 0.011 ml (0.13 mmol) of pyrrolidine was added to the reaction mixture and the mixture was stirred at 0° C. to room temperature for one hour. To the reaction mixture was added 1N hydrochloric acid, and the resulting mixture was extracted with chloroform. The chloroform layer was washed successively with a saturated aqueous solution of sodium hydrogencarbonate and a saturated aqueous solution of sodium chloride, dried over anhydrous sodium sulfate, and then concentrated under reduced pressure. The thus obtained crude product was purified by silica gel column chromatography (30 ml of silica gel, eluting solvent; n-hexane :ethyl acetate=1 :2) to give 19 mg (yield 65%) of Compound 15.

The physicochemical properties of Compound 15 are as follows:

$^1$H-NMR (400MHz, CDCl$_3$)δ(ppm): 9.36(1H, br. s), 9.06 (1H, br. s), 8.16(1H, s), 7.00(1H, d, J=2.3 Hz), 6.90(1H, s), 4.74(1H, dd, J=10.2, 1.0 Hz), 4.63 (1H, m), 4.55(1H, dd, J=10.1, 2.4 Hz), 4.08(3H, s), 3.97(3H, s), 3.95(3H, s), 3.92(3H, s), 3.81(1H, dd, J=10.4, 2.1 Hz), 3.67(2H, t, J=6.5 Hz), 3.52 (2H, t, J=6.6 Hz), 3.22(1H, dd, J=10.1, 10.1 Hz), 2.65(3H, s), 1.99(4H, m)

IR (KBr)ν(cm$^{-1}$): 3230, 2942, 1699, 1490, 1415, 1312, 1216, 1109

SIMS m/z : 671, 669(M+1)$^+$, 591, 234

EXAMPLE 15

Synthesis of Compound 16

Compound 1 (30 mg, 0.044 mmol) was dissolved in 6 ml of THF, and 0.053 ml (0.053 mmol) of 1.0 M THF solution of tetra-n-butylammonium fluoride was added to the solution, followed by stirring at room temperature for one hour. To the reaction mixture was added 0.2 M phosphate buffer (pH 7), and the resulting mixture was extracted with chloroform. The chloroform layer was washed with a saturated aqueous solution of sodium chloride, dried over anhydrous sodium sulfate, and then concentrated under reduced pressure. Acetonitrile (6 ml) and 0.1 ml of 48% hydrobromic acid were added to the resulting crude product, followed by stirring at room temperature for one hour. To the reaction mixture was added 0.2 M citrate buffer (pH 4), and the resulting mixture was extracted with chloroform. The chloroform layer was washed with a saturated aqueous solution of sodium chloride, dried over anhydrous sodium sulfate, and then concentrated under reduced pressure. The resulting crude product was dissolved in 3 ml of dichloromethane, and 0.012 ml (0.088 mmol) of triethylamine and 17.6 mg (0.088 mmol) of p-nitrophenyl chloroformate were added to the solution at −10° C., followed by stirring at −10° C. to 0° C. for one hour. Then, 0.015 ml (0.13 mmol) of N-methylpiperazine was added to the reaction mixture and the mixture was stirred at 0° C. to room temperature for 24 hours. To the reaction mixture was added 1N hydrochloric acid, and the resulting mixture was extracted with chloroform. The chloroform layer was washed successively with a saturated aqueous solution of sodium hydrogencarbonate and a saturated aqueous solution of sodium chloride, dried over anhydrous sodium sulfate, and then concentrated under reduced pressure. The thus obtained crude product was purified by silica gel column chromatography (30 ml of silica gel, eluting solvent; chloroform : methanol=50 :1) to give 18 mg (yield 58%) of Compound 16.

The physicochemical properties of Compound 16 are as follows:

$^1$H-NMR (400MHz, CDCl$_3$)δ(ppm): 9.34(1H, br. s), 8.81 (1H, br. s), 8.15(1H, s), 6.99(1H, d, J=2.3 Hz), 6.90(1H, s), 4.74(1H, dd, J=10.2, 1.2 Hz), 4.63 (2H, m), 4.08(3H, s), 3.97(3H, s), 3.95(3H, s), 3.92(3H, s), 3.82(1H, dd, J=9.9, 2.2 Hz), 3.78(2H, br), 3.64(2H, br), 3.23(1H, dd, J=10.0, 10.0 Hz), 2.70(3H, s), 2.50(4H, br), 2.37(3H, s)

IR (KBr)ν(cm$^{-1}$): 3475, 3232, 2944, 1698, 1491, 1410, 1313, 1217, 1110

SIMS m/z : 700, 698(M+1)+, 466, 464, 339, 234

EXAMPLE 16

Synthesis of Compound 17

Compound 1 (20 mg, 0.029 mmol) was dissolved in 2 ml of THF, and 0.044 ml (0.044 mmol) of 1.0 M THF solution of tetra-n-butylammonium fluoride was added to the solution, followed by stirring at room temperature for one hour. To the reaction mixture was added 0.2 M phosphate buffer (pH 7), and the resulting mixture was extracted with ethyl acetate. The ethyl acetate layer was washed with a saturated aqueous solution of sodium chloride, dried over anhydrous sodium sulfate, and then concentrated under reduced pressure. Acetonitrile (2 ml) and 1 ml of 6N hydrochloric acid were added to the resulting crude product, followed by stirring at room temperature for 2 hours. To the reaction mixture was added 0.2 M citrate buffer (pH 4), and the resulting mixture was extracted with ethyl acetate. The ethyl acetate layer was washed with a saturated aqueous solution of sodium chloride, dried over anhydrous sodium sulfate, and then concentrated under reduced pressure. Pyridine (2 ml) and 0.027 ml (0.29 mmol) of N,N-dimethylcarbamoyl chloride were added to the resulting crude product at 0° C. followed by stirring at 0° C. to room temperature for 24 hours. To the reaction mixture was added 1N hydrochloric acid, and the resulting mixture was extracted with chloroform. The chloroform layer was washed successively with a saturated aqueous solution of sodium hydrogencarbonate and a saturated aqueous solution of sodium chloride, dried over anhydrous sodium sulfate, and then concentrated under reduced pressure. The thus obtained crude product was purified by silica gel column chromatography (20 ml of silica gel, eluting solvent; chloroform :methanol=80 :1) to give 15 mg (yield 86%) of Compound 17.

The physicochemical properties of Compound 17 are as follows:

$^1$H-NMR (400MHz, CDCl$_3$)δ(ppm): 9.34(1H, br. s), 8.86 (1H, br. s), 8.16(1H, s), 6.99(1H, d, J=2.3 Hz), 6.89(1H, s), 4.77(1H, br. d, J=9.1 Hz), 4.55(2H, m), 4.09(3H, s), 3.95(3H, s), 3.94(4H, br. s), 3.92(3H, s), 3.35(1H, dd, J=10.0, 10.0 Hz), 3.20 (3H, s), 3.07(3H, s), 2.67(3H, s)

IR (KBr)ν(cm$^{-1}$): 2940, 1702, 1697, 1490, 1382, 1313, 1219, 1175, 1110

SIMS (m/z): 599(M+1)+, 366, 294, 234

EXAMPLE 17

Synthesis of Compound 18

Compound 16 (300 mg, 0.429 mmol) was dissolved in 30 ml of ethanol, and 5 ml of 5.88 N hydrogen chloride-methanol was added to the solution, followed by stirring at room temperature for one hour. The reaction mixture was concentrated under reduced pressure to give 279 mg (yield of Compound 18.

The physicochemical properties of Compound 18 are as follows:

$^1$H-NMR (400MHz, DMSO-$d_6$)$\delta$(ppm): 12.13(1H, br. s), 11.30(1H, d, J=1.0 Hz), 10.70(1H, br. s), 7.93 (1H, s), 7.00(1H, d, J=1.9 Hz), 6.97(1H, s), 4.65 (1H, dd, J=9.9, 9.9 Hz), 4.46(3H, m), 4.14(2H, br), 3.94(3H, s), 3.85(3H, s), 3.82(3H, s), 3.80 (3H, s), 3.58(2H, br), 3.49(4H, br), 3.41(1H, dd, J=9.3, 9.3 Hz), 2.84(3H, br. s), 2.69(3H, s)

IR (KBr)$\nu$(cm$^{-1}$): 2948, 1719, 1697, 1609, 1492, 1414, 1312, 1220, 1168, 1109, 1088

EXAMPLE 18

Synthesis of Compound 19

Compound 19 (19 mg, yield 66%) was obtained from 30 mg (0.044 mmol) of Compound 1 in a similar manner as in Example 15 except that 6 N hydrochloric acid was used instead of 48% hydrobromic acid.

The physicochemical properties of Compound 19 are as follows:

IR (KBr)$\nu$(cm$^{-1}$): 2940, 1698, 1637, 1491, 1410, 1314, 1218, 1154, 1109

SIMS m/z: 654(M+1)+, 420, 234

EXAMPLE 19

Synthesis of Compound 20

Compound 19 (17 mg, 0.026 mmol) was dissolved in ml of ethanol, and 0.04 ml of 5.8N hydrogen chloride-ethanol was added to the solution, followed by stirring at room temperature for one hour. The reaction mixture was concentrated under reduced pressure to give 18 mg (yield 100%) of Compound 20.

The physicochemical properties of Compound 20 are as follows: $^1$H-NMR (400MHz, DMSO-$d_6$)$\delta$(ppm): 12.13(1H, br. s), 11.30(1H, br. s), 10.72(1H, br. s), 7.93(1H, s), 7.00(1H, d, J=2.0 Hz), 6.96(1H, s), 4.65(1H, dd, J=10.2, 9.6 Hz), 4.43(3H, m), 4.15(2H, br), 3.94 (3H, s), 3.85(3H, s), 3.82(3H, s), 3.80(3H, s), 3.61(2H, br), 3.51(5H, br), 2.84(3H, br. s), 2.69 (3H, s)

IR (KBr)$\nu$(cm$^{-1}$): 2946, 1700, 1609, 1527, 1491, 1410, 1313, 1217, 1172, 1109, 1090

REFERENCE EXAMPLE 1

*Streptomyces lydicus* DO-89 (FERM BP-988) was used as the seed strain. The strain was inoculated into 200 ml of a seed medium [25 g/l soluble starch, 5 g/l glucose, 1 g/l yeast extract, 10 g/l Peptone-A (Kyokuto Pharmaceutical Co., Ltd.) and 1 g/l calcium carbonate; pH 7.2 before sterilizationg] in a 2-l Ehrlenmeyer flask and subjected to shaking culture (200 r.p.m.) at 28° C. for 48

The resulting seed culture was transferred to a 30-l jar fermenter containing 15 l of a medium having the same composition as the above seed medium at a rate of 5% (by volume) and cultured with stirring and aeration (rotation: 200 r.p.m., aeration: 15 l/min) at 28° C. for 24 hours. The obtained culture was transferred to a 200-l tank fermenter containing 150 l of a fermentation medium having the following composition at a rate of 10% (by volume) and cultured with stirring and aeration (rotation: 200 r.p.m., aeration: 15 l/min) at 28° C.

Composition of the fermentation medium: 50 g/l maltose, 15 g/l dry yeast, 25 g/l Ebios (Asahi Breweries, Ltd.), 10 g/l KCl, 0.5 g/l KH$_2$PO$_4$, 0.5 g/l MgSO$_4$.7H$_2$O, 5 g/l calcium carbonate (pH 5.0; adjusted with 6N H$_2$SO$_4$ prior to sterilization).

Culturing was carried out for 100 hours without controlling the pH of the medium. The cells and the precipitate were separated from the culture by filtration to give 100 l of a filtrate. To the cells and the precipitate was added 50 l of n-propanol, and after being stirred well, the mixture was filtered to give 45 l of n-propanol extract. The culture filtrate and the n-propanol extract were combined (total volume: 140 l), and the mixture was passed through 5 l of Diaion HP-20 (Mitsubishi Kasei Corporation) to adsorb the active component. After the column was washed with water and then with 70% aqueous methanol, elution was carried out with methanol. The methanol-eluted fractions were concentrated and the concentrate was extracted with 10 l of ethyl acetate. The ethyl acetate extract was concentrated, and n-hexane was added to the concentrate to give a crude powder of DC-89A2. The crude powder of DC-89A2 was then recrystallized from methanol to give 1 g of pure DC-89A2.

REFERENCE EXAMPLE 2

Culturing was carried out in a similar manner as in Reference Example 1 except that the fermentation medium having the following composition was used.

Composition of the fermentation medium: 50 g/l maltose, 15 g/l dry yeast, 25 g/l Ebios (Asahi Breweries, Ltd.), 10 g/l KBr, 0.5 g/l KH$_2$PO$_4$, 0.5 g/l MgSO$_4$.7H$_2$O, 5 g/l calcium carbonate (pH 5.0; adjusted with 6N H$_2$SO$_4$ prior to sterilization).

After the pH of the resulting culture was adjusted to 4.5 with 12N HCl, the cells and the precipitate were separated from the culture by filtration to give 100 l of a filtrate. To the cells and the precipitate was added 50 l of n-propanol, and after being stirred well, the mixture was filtered to give 45 l of n-propanol extract. The culture filtrate and the n-propanol extract were combined (total volume: 140 l), and the mixture was passed through 5 l of Diaion HP-20 (Mitsubishi Kasei Corporation) to adsorb the active component. After the column was washed with water and then with 70% aqueous methanol, elution was carried out with methanol to give the methanol-eluted fractions containing DC-89B1 and the methanol-eluted fractions containing DC-89B2. The fractions containing DC-89B1 were concentrated and the concentrate was passed through 200 ml of Diaion HP-20SS (Mitsubishi Kasei Corporation), followed by elution with 80% aqueous methanol of pH 4.0. The eluted fractions containing DC-89B1 were concentrated and the concentrate was extracted with ethyl acetate. The ethyl acetate extract was concentrated, and n-hexane was added to the concentrate to give 0.5 g of pure DC-89B1.

The methanol-eluted fractions containing DC-89B2 were concentrated and the concentrate was passed through 500 ml of Diaion HP-20SS (Mitsubishi Kasei Corporation), followed by elution with 85% aqueous methanol of pH 4.0. The eluted fractions containing DC-89B2 were concentrated and the concentrate was extracted with ethyl acetate. The ethyl acetate extract was concentrated, and n-hexane was added to the concentrate to give a crude powder of DC-89B2. The crude powder of DC-89B2 was recrystallized from methanol to give 1.5 g of pure DC-89B2.

REFERENCE EXAMPLE 3

Synthesis of Compound (e)

DC-89B2 obtained in Reference Example 2 (123 mg) and 43 mg of imidazole were dissolved in 3.0 ml of DMF, and 50 mg of t-butyldimethylsilyl chloride was added to the solution under ice-cooling. After stirring for 4 hours and 30 minutes, 2N hydrochloric acid solution was added to the reaction mixture, and the resulting mixture was extracted with ethyl acetate. The ethyl acetate layer was washed successively with a saturated aqueous solution of sodium hydrogencarbonate and a saturated aqueous solution of sodium chloride, and dried over anhydrous sodium sulfate. The solvent was removed by distillation under reduced pressure, and the residue was purified by silica gel column chromatography (30 ml of silica gel, eluting solvent; n-hexane : ethyl acetate=3 :1) to give 140 mg (yield 95%) of Compound (e).

The physicochemical properties of Compound (e) are as follows:

$^1$H-NMR (400MHz, CDCl$_3$)$\delta$(ppm): 9.38(1H, br. s), 8.23 (1H, br. s), 6.95(1H, d, J=2.2 Hz), 6.87(1H, s), 5.04(1H, br), 4.62(1H, dd, J=10.6, 9.1 Hz), 4.54 (1H, dd, J=10.6, 4.4 Hz), 4.17(1H, m), 4.06(3H, s), 4.06(1H, dd, J=10.3, 3.0 Hz), 3.99(3H, s), 3.91(3H, s), 3.78(3H, s), 3.57(1H, dd, J=9.8, 9.1 Hz), 1.69 (3H, s), 1.06(9H, s), 0.36(3H, s), 0.35(3H, s)

IR (KBr)$\nu$(cm$^{-1}$): 1745, 1700, 1618, 1497, 1293, 837

REFERENCE EXAMPLE 4

Synthesis of Compound (a)

Compound (e) obtained in Reference Example 3 (155 mg, 0.22 mmol) was dissolved in 7 ml of allyl alcohol, and 25 mg (0.66 mmol) of sodium borohydride was added to the solution under ice-cooling, followed by stirring for 2 hours and 40 minutes. The reaction mixture was poured into 2N hydrochloric acid and the mixture was extracted with chloroform. The chloroform layer was washed successively with a saturated aqueous solution of sodium hydrogencarbonate and a saturated aqueous solution of sodium chloride, dried over anhydrous sodium sulfate, and then concentrated under reduced pressure. The thus obtained crude product was purified by silica gel column chromatography (50 ml of silica gel, eluting solvent; n-hexane : ethyl acetate=3 :1 to 1 :1) to give 115 mg (yield 74%) of Compound (a).

The physicochemical properties of Compound (a) are as follows:

$^1$H-NMR (400 MHz, CDCl$_3$)$\delta$(ppm): 9.43(1H, br. s), 7.91 (1H, br. s), 6.91(1H, d, J=2.2 Hz), 6.86(1H, s), 5.31(1H, br. s), 4.57(1H, dd, J=10.6, 8.9 Hz), 4.50(1H, dd, J=10.6, 3.9 Hz), 4.07(1H, dd, J=10.3, 3.2 Hz), 4.05(3H, s), 3.93(3H, s), 3.92(1H, m), 3.91(3H, s), 3.72(3H, s), 3.49(1H, dd, J=10.1, 9.8 Hz), 2.09(1H, br. s), 1.60(3H, s), 1.04(9H, s), 0.32(3H, s), 0.30(3H, s)

IR (KBr)$\nu$(cm$^{-1}$): 3406, 1734, 1621, 1485, 1111, 838

SIMS m/z: 706, 704(M+1)

REFERENCE EXAMPLE 5

Synthesis of Compound (a) and Compound (b)

Compound (e) (200 mg, 0.28 mmol) was dissolved in 5 ml of methanol, and 23 mg (0.61 mmol) of sodium borohydride was added to the solution under ice-cooling, followed by stirring at room temperature for 2 hours and minutes. The reaction mixture was poured into 2N hydrochloric acid and the mixture was extracted with chloroform. The chloroform layer was washed successively with a saturated aqueous solution of sodium hydrogencarbonate and a saturated aqueous solution of sodium chloride, dried over anhydrous sodium sulfate, and then concentrated under reduced pressure. The thus obtained crude product was purified by silica gel column chromatography (100 ml of silica gel, eluting solvent; n-hexane :ethyl acetate=4 :1 to 2 :1) to give 81 mg (yield 40%) of Compound (a) and 12 mg (yield 6.5%) of Compound (b).

The physicochemical properties of Compound (b) are as follows:

$^1$H-NMR (400MHz, CDCl$_3$) 6(ppm): 9.43(1H, br. s , 7.87 (1H, br. s), 6.88(1H, d, J=2.2 Hz), 6.85(1H, s), 4.90(1H, d, J=5.7 Hz), 4.55(1H, dd, J=10.3, 9.3 Hz), 4.40(1H, dd, J=10.8, 5.2 Hz), 4.05(1H, m), 4.05 (3H, s), 3.93(3H, s), 3.89(3H, s), 3.81(1H, dd, J=10.1, 3.4 Hz), 3.71(1H, m), 3.49(1H, dd, J=10.1, 9.6 Hz), 1.37(1H, d, J=6.9 Hz), 1.01(9H, s), 0.30 (3H, s), 0.29(3H, s)

IR (KBr)$\nu$(cm$^{-1}$): 3450, 2934, 1618, 1486, 1309, 840

EIMS m/z: 629, 627(M-H$_2$O)

REFERENCE EXAMPLE 6

Synthesis of Compound (c)

Compound (e) (300 mg, 0.43 mmol) was dissolved in 10 ml of isopropyl alcohol, and 26 mg (0.69 mmol) of sodium borohydride was added to the solution under ice-cooling, followed by stirring at room temperature for 10 hours. The reaction mixture was poured into 2N hydrochloric acid and the mixture was extracted with chloroform. The chloroform layer was washed successively with a saturated aqueous solution of sodium hydrogencarbonate and a saturated aqueous solution of sodium chloride, dried over anhydrous sodium sulfate, and then concentrated under reduced pressure. The thus obtained crude product was purified by silica gel column chromatography (50 ml of silica gel, eluting solvent; n-hexane :ethyl acetate=3 :1) to give 55 mg (yield 18%) of Compound (c) and 128 mg (yield 42%) of Compound (a).

The physicochemical properties of Compound (c) are as follows:

$^1$H-NMR (100MHz, CDCl$_3$)$\delta$(ppm): 9.43(1H, br. s , 7.90 (1H, s), 6.90(1H, d, J=2.3 Hz), 6.86(1H, s), 5.31 (1H, d, J=10.4 Hz), 4.98(1H, m), 4.7–4.4(2H, m), 4.2–3.7(2H, m), 4.04(3H, s), 3.92(3H, s), 3.90 (3H, s), 3.45(1H, t, J=9.2 Hz), 2.09(1H, d, J=10.0 Hz), 1.22(3H, d, J=6.4 Hz), 1.18(3H, d, J=6.4 Hz), 1.04(9H, s), 0.31(3H, s), 0.28(3H, s)

REFERENCE EXAMPLE 7

Synthesis of Compound (d)

Compound (e) (72.4 mg, 0.10 mmol) was dissolved in 3.6 ml of benzyl alcohol, and 14.2 mg (0.10 mmol) of anhydrous potassium carbonate was added to the solution, followed by stirring at room temperature for 20 hours. After addition of 206 μl (0.21 mmol) of 1N hydrochloric acid under ice-cooling, 16.6 mg (0.44 mmol) of sodium borohydride was added to the reaction mixture, and the resulting mixture was stirred for 2 hours. Then, 1N hydrochloric acid was added to the reaction mixture, followed by extraction with ethyl acetate. The ethyl acetate layer was washed successively with a saturated aqueous solution of sodium hydrogencarbonate and a saturated aqueous solution of sodium chloride, dried over anhydrous sodium sulfate, and then concentrated under reduced pressure. Benzyl alcohol was removed from the resulting crude product by azeotropic distillation with t-butylbenzene, and the product was purified by silica gel column chromatography (22 ml of silica gel, eluting solvent; n-hexane :ethyl acetate =4 :1) to give 40.3 mg (yield 50%) of Compound (d).

The physicochemical properties of Compound (d) are as follows:

$^1$H-NMR (100MHz, CDCl$_3$) δ (ppm): 9.40(1H, br. s), 7.84 (1H, s), 7.4–7.1(5H, m), 6.84(1H, d, J=2.3 Hz), 6.80(1H, s), 5.27(1H, d, J=9.6 Hz), 5.07(2H, s), 4.7–4.3(3H, m), 4.1–3.7(1H, m), 4.00(3H, s), 3.89(3H, s), 3.86(3H, s), 3.42(1H, t, J=9.0 Hz), 2.13(1H, d, J=9.6 Hz), 1.59(3H, s), 1.02(9H, s), 0.30(3H, s), 0.27(3H, s)

IR (KBr)ν(cm$^{-1}$): 3450, 2936, 1730, 1623, 1483, 1311, 838

EIMS m/z: 781, 779(M+), 701, 699, 548, 546, 448, 396, 394, 314, 234, 91

What is claimed is:

1. A compound represented by the formula:

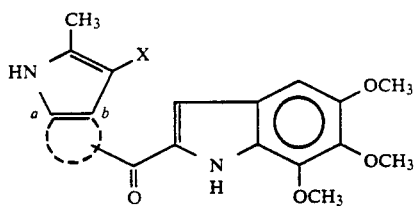

wherein X represents hydrogen or $CO_2R^1$ (in which $R^1$ represents hydrogen, a straight-chain or branched alkyl having 1 to 4 carbon atoms, allyl, or benzyl); and

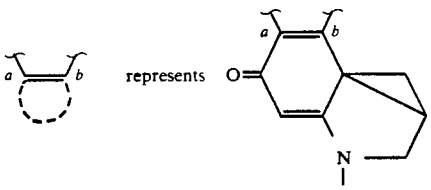

2. A compound according to claim 1, wherein X represents $CO_2R^1$.

3. A compound according to claim 2, wherein $R^1$ represents a straight-chain or branched alkyl having 1 to 3 carbon atoms.

4. A compound according to claim 3, wherein $R^1$ represents methyl.

5. A pharmaceutical composition comprising a pharmaceutical carrier and, as an active ingredient, the derivative as defined by claim 1.

* * * * *

UNITED STATES PATENT AND TRADEMARK OFFICE
CERTIFICATE OF CORRECTION

PATENT NO. : 5,187,186
DATED : February 16, 1993
INVENTOR(S) : YUTAKA KANDA, ET AL.

It is certified that error appears in the above-identified patent and that said Letters Patent is hereby corrected as shown below:

COLUMN 4

Line 22, "R9" should read --$R^9$--.
Line 27, "dimethylformaxide" should read --dimethylformamide--.

COLUMN 5

Line 66, "↓Step" should read --↓Step 4--.

COLUMN 7

Line 19, "Compound (I-4)" should read --¶ Compound (I-4)--.

COLUMN 10

Line 4, "1 to" should read --1 to 2--.
Line 60, "Compound (I)," should read --Compounds (I),--.

COLUMN 13

Line 6, "Ond" should read --One--.

COLUMN 14

Line 61, "685($M^{30}$)," should read --685($M^+$),--.

COLUMN 15

Line 14, "Physicochemical" should read --physicochemical--.

UNITED STATES PATENT AND TRADEMARK OFFICE
CERTIFICATE OF CORRECTION

PATENT NO. : 5,187,186

DATED : February 16, 1993

INVENTOR(S) : YUTAKA KANDA, ET AL.

It is certified that error appears in the above-identified patent and that said Letters Patent is hereby corrected as shown below:

COLUMN 17

Line 59, "6 (ppm):" should read --δ (ppm):--.

COLUMN 18

Line 5, "mg" should read --55 mg--.
Line 6, close up left margin.
Line 9, "6 (ppm):" should read --δ (ppm):--.

COLUMN 19

Line 18, "761(M+)," should read --761($M^+$),--.
Line 68, "643(M+1)+," should read --643(M+1)$^+$,--.

COLUMN 22

Line 21, "698(M+1)+," should read --698(M+1)$^+$,--.
Line 66, append line 66 to line 65 and close up left margin of line 66.

COLUMN 23

Line 10, "(yield" should read --(yield 88%)--.
Line 38, "ml" (first occurrence) should read --1 ml--.
Line 44, "$^1$H-NMR" should read --¶ $^1$H-NMR--.
Lines 58-59, "carbonate; pH 7.2 before sterilizationg]" should read --carbonate (pH 7.2; before sterilization)]--.
Line 60, "48" should read --48 hours.--.

UNITED STATES PATENT AND TRADEMARK OFFICE
CERTIFICATE OF CORRECTION

PATENT NO.  : 5,187,186
DATED       : February 16, 1993
INVENTOR(S) : YUTAKA KANDA, ET AL.

It is certified that error appears in the above-identified patent and that said Letters Patent is hereby corrected as shown below:

<u>COLUMN 26</u>

Line 5, "ml" should read --12 ml--.
  Line 8, "minutes." should read --40 minutes.--.
  Line 22, "6 (ppm):" should read --δ (ppm):-- and
           "(1H, br. s," should read --(1H, br. s),--.
  Line 53, "(1H, br. s," should read --(1H, br. s),--.

<u>COLUMN 27</u>

Line 21, "6 (ppm):" should read --δ (ppm):--.
  Line 30, "779(M+)," should read --779(M$^+$),--.

<u>COLUMN 28</u>

Line 23, insert: --or a pharmaceutically acceptable
                   salt thereof.--.

Signed and Sealed this

Eighth Day of February, 1994

BRUCE LEHMAN

Attest:

Attesting Officer

Commissioner of Patents and Trademarks